United States Patent [19]

Smid et al.

[11] Patent Number: 5,256,334

[45] Date of Patent: Oct. 26, 1993

[54] HOMOGENEOUS RADIOPAQUE POLYMER-ORGANOBISMUTH COMPOSITES

[75] Inventors: Johannes Smid, Lafayette; Yadollah Delaviz; Israel Cabasso, both of Syracuse, all of N.Y.

[73] Assignee: The Research Foundation of the State University of New York, Albany, N.Y.

[21] Appl. No.: 843,126

[22] Filed: Feb. 28, 1992

Related U.S. Application Data

[63] Continuation of Ser. No. 619,026, Nov. 28, 1990, abandoned, which is a continuation of Ser. No. 243,246, Sep. 8, 1988, abandoned.

[51] Int. Cl.$^5$ .............................................. C08F 4/06
[52] U.S. Cl. .................................. 252/478; 433/228.1; 523/117
[58] Field of Search ................... 252/478; 433/228.1; 523/117

[56] References Cited

U.S. PATENT DOCUMENTS

| | | | |
|---|---|---|---|
| 2,833,741 | 5/1958 | Lal | 260/45.5 |
| 3,485,919 | 12/1969 | Markgraf et al. | 424/322 |
| 3,577,346 | 5/1971 | McKeown et al. | 252/63.5 |
| 3,609,372 | 9/1971 | Vogel | 250/108 |
| 3,890,242 | 6/1975 | Curry | 252/109 |
| 3,901,829 | 8/1975 | Slingluff et al. | 252/478 |
| 3,974,104 | 8/1976 | Foster et al. | 252/478 |
| 4,129,524 | 12/1978 | Nagai et al. | 252/478 |
| 4,138,361 | 2/1979 | Suys et al. | 252/301.33 |
| 4,250,072 | 2/1981 | Flynn | 260/31.2 |
| 4,282,876 | 8/1981 | Flynn | 128/349 R |
| 4,283,447 | 8/1981 | Flynn | 428/36 |
| 4,429,094 | 1/1984 | Massucco | 526/240 |
| 4,500,658 | 2/1985 | Fox | 523/117 |
| 4,503,169 | 3/1985 | Randkley | 523/117 |
| 4,517,793 | 5/1985 | Carus et al. | 57/243 |
| 4,522,868 | 6/1985 | Ohuchi et al. | 428/224 |
| 4,525,147 | 6/1985 | Pitz et al. | 433/224 |
| 4,581,390 | 4/1986 | Flynn | 523/112 |
| 4,584,326 | 4/1986 | Flynn | 523/112 |
| 4,655,588 | 4/1987 | Sayles | 149/19.92 |
| 4,736,684 | 4/1988 | Byrd et al. | 102/290 |

OTHER PUBLICATIONS

J. Smid, I. Cabasso, A. Obligin, and S. E. Sahini, "Novel Polymer-Salt Systems For X-Ray Imaging", 1987, pp. 133, 134.

C.A., vol. 51, 1957, p. 10126, "Improved polymerization of formaldehyde," E. I. duPont de Nemours & Co.

*Primary Examiner*—Marianne M. Cintins
*Assistant Examiner*—Catherine Scalzo
*Attorney, Agent, or Firm*—Morgan & Finnegan

[57] ABSTRACT

Novel radiopaque materials and a method for their preparation are described. The radiopaque materials comprise composites of polymers and heavy metal-containing organic compounds, which heavy metal containing compounds have the following formula:

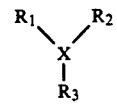

wherein X is a heavy metal; $R_1$, $R_2$ and $R_3$ may be the same or different and are individually selected from the group consisting of phenyl, halogen substituted phenyls, alkyl substituted phenyls, aryl substituted phenyls, ester substituted phenyls, alkene substituted phenyls, silyl groups and methylmethacrylate and $R_3$ can additionally be selected from the group consisting of halogen, alkyl, alkene, ester and carboxylic acid when $R_3$ is not the same as $R_1$ and $R_2$.

The composites, which are permanent and nonleachable, do not adversely affect the mechanical and physical properties of compositions. They are useful as medical and dental resins, in fabricating medical and dental appliances, prosthetic devices, radiation shielding devices and radiopaque polyester fabrics for clothing.

3 Claims, No Drawings

OTHER PUBLICATIONS

C.A., vol. 52, 1958, p. 14219. "Polymerization of acrylate esters in the presence of organometallic inhibitors." Lal.

C.A., vol. 57, 1962, p. 15147. "Synthesis of organobismuth compounds through diaryliodonium salts." Ptitsyna, et al.

C.A. vol. 51, 1957, p. 4057. "Curing polyepoxides and products therefrom". Shokal.

C.A., vol. 56, 1962, p. 3654. "Catalysts for the low-pressure polymerization of ethylene." Union Carbide Corp.

C.A., vol. 62, 1965, p. 16300. "New organobismuth compounds." M&T Chemical Inc.

C.A., vol. 63, 1965, p. 5772. "Polymerization catalyst mixture of bismuth, cuprous salt and Lewis acid." Feay, et al.

C.A., vol. 69, 1968, 78425m. "Neomycin and organobismuth antibacterial finish for cellulose material." Gross.

C.A., vol. 71, 1969, 82057b. "Nonforaminous polychloral." Vogl.

C.A., vol. 77, 1972, 20422g. "Catalytic manufacture of polyamides." Jones, et al.

C.A., vol. 71, 1969, 81937b. "Direct esterification of aromatic dicarboxylic acids with glycols with bismuth compounds as catalysts for use in production of polymers." Muller.

C.A., vol. 73, 1970, 102077e. "Anthelmintic bismuth compounds." Saagers.

C.A., vol. 76, 1972, 15381t. "Organobismuth antoxidants for organic polymers." Ohseki, et al.

C.A., vol. 77, 1972, 76842m. "Insulated electrical conductors having corona resistant polymeric insulation containing organo metallic compounds." McKeown.

C.A. vol. 87, 1977, 87:93583b. "Radiation-produced colored photopolymer systems." Lewis, et al.

C.A. vol. 90, 1979, 90:46612n. "Radiation-sensitive resist-forming composition." Wagner, et al.

C.A., vol. 97, 1982, 97:130013v. "XLDB binder catalysis studies." Haas, et al.

C.A., vol. 89, 1978, 89:25461b. "Molding compositions." Graham et al.

C.A., vol. 92, 1980, 92:67716f. "Photo imaging compositions." Endo, et al.

C.A., vol. 98, 1983, 98:136954v. "Detection of organometallic complexes in an organic matrix by lasar microprobe spectrometry." Ollman, et al.

HOMOGENEOUS RADIOPAQUE POLYMER-ORGANOBISMUTH COMPOSITES

This invention was made with Government support under research Grant No. NIH-1-RO1-DEO61790-01A1 awarded by the National Institutes of Health. The Government has certain rights in this invention.

This is a continuation of application Ser. No. 07/619,026, filed Nov. 28, 1990, now abandoned, which is a continuation of application Ser. No. 07/243,246 filed Sep. 8, 1988, now abandoned.

BACKGROUND OF THE INVENTION

The present invention relates to new and useful polymers, and more specifically, to improved nonleachable, optically transparent, homogeneous radiopaque heavy metal-containing polymers, compositions of matter, their method of preparation and articles prepared therefrom.

Translucent polymeric materials, and particularly, acrylic type resins have been widely used for years in both medical and dental applications. In dentistry, for example, resins have been used to produce removable dentures, temporary crown and bridge materials, restorative materials, impression materials, and the like. Polymeric resins also find many applications in medicine, such as surgical and body implants and other prosthetic devices, (e.g., heart valves, blood vessels, etc.). Translucent plastics are also widely used in medical appliances, such as catheters.

The desirability of imparting radiopacity to plastics used in dentistry and medicine has long been recognized. In dentistry for example, it has been difficult to detect secondary cavities or underlying decalcified dentin resulting from the placement of unreinforced direct restorative resins because these materials are relatively radiolucent, and are not opaque to x-rays. Surveys have also shown that dental instruments, materials and nonfixed appliances have fractured and become embedded in soft tissues, ingested or inhaled inadvertently by patients. Although incidents of ingestion or inhalation of dental plastics are relatively rare compared with other foreign objects, the occurrence may result in a severe medical emergency or even death. The potential severity of such an incident makes it imperative to diagnose and remove such foreign bodies rapidly.

In medicine, it would be desirable to monitor the positioning of bone cement used in hip joint replacements without surgical procedure. Similarly, it would be desirable to use x-rays to monitor replacement heart valves, replacement arteries, or the path of catheters traversing blood vessels and organ systems. Hence, there is a need for polymeric materials with increased radiation absorption potentials which also possess the requisite nonleachable properties for safe and acceptable use in dentistry and medicine.

Heavy metal salts, such as, for example, those of bismuth or barium have been used as contrast medium in diagnostic radiography. They have properties which would suggest their suitability for increasing the radiation absorption potential of medical and dental resins. As a result, substantial effort has been made to incorporate barium sulfate and other radiopaque salts, such as, for example, bismuth bromide, bismuth chloride or bismuth subnitrate into polymers to render them opaque to x-rays. However, early radiopaque polymers containing heavy metal salts have not been totally satisfactory.

One type of known heavy metal-containing radiopaque materials are radiopaque glass containing embedded heavy metals. In these materials, the metal is not molecularly bound to the polymer matrix and, therefore, has a tendency to weaken the composite. Moreover, because glass filler based resins lack homogeneity a further weakening of regions in the matrix results. Those regions of a composite having little or no glass are radiolucent. In addition, a light scattering effect is produced by radiopaque glasses which alters optical properties and renders them optically opaque.

Polymers with added inorganic heavy metal salts in an essentially physical mixture, are also known. In these materials the heavy metal is present as fine powders locked in a matrix. Their preparation results in an uneven distribution of the salt, which has an adverse affect on the mechanical properties of the plastic material. The salt tends to gradually leach out of the matrix causing discoloration of the polymer and release of heavy metal toxins. The salt and polymer remain as separate distinct phases in these mixtures producing an opaque, cloudy, light scattering material. Mixing does not impart homogeneity between the salt and polymer.

More recently, heavy metal salts have been complexed with a polymer. Such composites require that the complexing polymer contain at least one monomer which is capable of donating a pair of electrons, i.e., acting as a Lewis base. These materials are, therefore, limited in structure since only polymers containing appropriate interaction sites, especially carbonyl moieties, are useful. These heavy metal-salt-polymer complexes are usually moisture sensitive. That is, an initially clear complex will cloud or turn milky upon exposure to moisture, making them inappropriate for certain applications. These heavy metal salt-polymer complexes may also be heat sensitive, and interfere with room temperature curing accelerators used in dental and other applications.

OBJECTS OF THE INVENTION

It is therefore an object of this invention to provide a means for imparting radiopaque characteristics to a wide range of polymers.

It is a further objective of this invention to provide radiopaque composites containing heavy metal atoms which are evenly distributed within a polymer.

A further objective of this invention is to provide radiopaque composites wherein a heavy metal containing organic compound is incorporated into the polymer chain thereby imparting radiopaque characteristics to the polymer.

It is also an objective of this invention to provide non-leachable, moisture insensitive and heat insensitive radiopaque composites which do not interfere with room temperature curing accelerators of the types used in dental applications.

It is also an objective of this invention to provide composites which are non-toxic and non-carcinogenic.

A still further objective of this invention is to provide composites in which the radiopacifying or x-ray contrast additive may also act as a bactericide, fungicide, antioxidant or stabilizer.

These and other benefits will be apparent to those skilled in the art from the following description and Examples.

DETAILED DESCRIPTION OF THE INVENTION.

It has now been found that these objectives can be attained by carrying out polymerization of a monomer or mixture of monomers in the presence of a heavy metal containing organic compound. The heavy metal containing organic compound has the general formula:

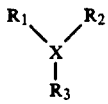

wherein X is a heavy metal; $R_1$, $R_2$ and $R_3$ may be the same or different and are individually selected from the group consisting of phenyl, halogen substituted phenyls, alkyl substituted phenyls, aryl substituted phenyls, ester substituted phenyls, alkene substituted phenyls, silyl groups and methylmethacrylate and $R_3$ can additionally be selected from the group consisting of halogen, alkyl, alkene, ester and carboxylic acid when $R_3$ is not the same as $R_1$ and $R_2$.

Heavy metals useful in this invention have atomic numbers of 50 to 92, and more preferrably, atomic numbers of 72 to 92. Lanthanide series metals having atomic numbers of 57 to 71, although satisfactory, are less preferred than the higher atomic weight metals like mercury, lead and bismuth. Rare transition metals with atomic numbers of 72 to 77 are also acceptable, but are less preferred because of lower atomic weights, high cost and their ability to form multinuclear complexes. Most preferred heavy metals include barium, bismuth, lead, mercury and uranium.

The heavy metal containing organic compounds useful in the present invention are relatively non-polar and are thus hydrophobic. This provides radiopaque composites that are moisture insensitive. These organometallic compounds are also miscible up to 70 weight percent with many polymers.

A preferred organometallic compound useful in this invention is triphenyl bismuth. Known uses for triphenyl bismuth include bactericide, fungicide, antioxidant and stabilizer. While the addition of triphenyl bismuth to polymers to form composites having radiopaque characteristics is a novel aspect of the present invention, the triphenyl bismuth component of the novel composite may also impart some bactericide, fungicide, antioxidant or stabilizing characteristics to the composite.

In one aspect, the present invention provides radiopaque materials which comprise a heavy metal containing organic compound as a radiopacifying agent miscible with a polymer at the molecular level. That is, instead of a physical, incompatible mixture of radiopacifying agent and polymer resulting in uneven distributions of radiopacifying agent which adversely affect mechanical and physical properties, according to the present invention a heavy metal containing organic compound, such as an organobismuth compound, is homogeneously solubilized into a polymer during polymerization of the corresponding monomer in which the radiopacifying compound is also soluble. The hydrophobic nature of the compound prevents its leaching out from a polymer matrix of the polymer into an aqueous environment.

In another aspect, this invention provides radiopaque materials comprising a heavy metal containing organic compound incorporated directly into a polymer chain. For example, by employing organometallic compounds in which one or more of the $R_1$, $R_2$, $R_3$ substituents is a polymerizable group, such as, for example, a styryl substituent, the polymerization of a monomer in the presence of such a compounds in accordance with this invention produces a material in which the organometallic compound is incorporated directly into the backbone of the polymer chain to provide distribution of the organobismuth compound on the molecular level, thereby producing a homogeneous composite. Since the organometallic compound is actually part of the polymer chain, the heavy metal radio-pacifying agent is non-leachable.

The polymer composite may be formed from any monomer or mixture of monomers into which the selected organometallic compound can be solubilized. It may also be formed by casting a homogeneous mixture of the polymer and the radiopacifying agent from an appropriate solvent. The method of imparting radiopaque characteristics of this invention has a much wider range of structures and applications than the heavy metal salts previously mentioned. The latter are essentially only useful with carbonyl-containing monomers and polymers, while the more hydrophobic organobismuth and related compounds are soluble in a much wider range of monomers and polymers. Useful polymers and mixtures of polymers include those derived from styrene, vinyl halides, alkenes, (e.g., polypropylene), dienes vinylpyridines, those derived from, acrylonitrile, vinyl acetate, acrylates and the like.

The organometallic compound can also be mixed, or incorporated into condensation polymers. They include linear and cross-linked types formed from dicarboxylic acids and diols or triols. Specific representative examples of polyesters include polyethylene terephthalate, poly (isophthalic acid-co-maleic anhydride), poly (lauric acid-co-glycerol), and the cross-linked resin poly (phthalic anhydride-co-glycerol) (glyptal). The polyester composite fibers of this invention are especially of interest for making fabrics for clothing to be worn by workers exposed to potentially harmful levels of radiation, such as radiologists and x-ray technicians.

The heavy metal containing organic compound should be present in an amount sufficient to impart a desired radiopacity to the polymer. The relative amounts of the components of the composites of this invention depend largely upon the specific heavy metal containing organic compound utilized, the specific polymer or mixture of polymers, the dimensions of the final product and the amount of radiopacity to be imparted to the polymer.

As previously mentioned, the heavy metals of the present invention are homogeneously distributed in the polymer at the molecular level to form optically lucent radiopaque materials. The hydrophobic nature of the heavy metal compound renders them virtually non-leachable from the resin into an aqueous environment to which the composites of this invention may be exposed. Non-leachability into many other solvents may be achieved by incorporating a polymerizable radiopacifying agent into the polymer backbone, either by addition polymerization or by condensation polymerization.

The present invention also contemplates the addition of cross-linking agents. This will provide even greater resistance to leaching of the heavy metal compound from the polymer. Suitable representative examples of cross-linking agents include tetraethylene glycol dimethacrylate (TEG), divinylbenzene, bisphenol-A-glycidyl methacrylate (BisGMA), and the like.

The linear radiopaque polymeric materials have molecular weights generally ranging from 10,000 to about 1,000,000, and more specifically, from about 25,000 to about 500,000.

Generally, the methods for preparing the homogeneous radiopaque polymers of the present invention include: a) bulk polymerization at high temperatures; b) room temperature polymerization; c) suspension or emulsion polymerization; d) solvent casting; and e) compounding followed by melt processing.

Bulk polymerization involves dissolving the heavy metal compound in the monomer(s) and polymerizing in the presence of an initiator like benzoyl peroxide, azobisisobutyronitrile (AIBN), etc. More specifically, in the preparation of radiopaque polymers having carbon to carbon unsaturation, such as a vinyl group, the heavy metal compound and an initiator are dissolved in the monomer, such as, for example, styrene, and bulk polymerized at elevated temperatures. This high temperature bulk method is especially adaptable for industrial uses. In polymerizations for molds or in vitro applications, for example, the heavy metal organic compounds can be dissolved in styrene and polymerized with AIBN at the desired temperature.

Room temperature polymerization can be utilized in this invention since, unlike the bismuth salts previously used to impart radiopacity, the radiopacifying organometallic compounds of this invention do not interfere with the room temperature polymerizations in which a peroxide initiator is used jointly with amine accelerators such as N,N-dimethyl-p-toluidine. Room temperature polymerization can also be initiated without accelerators by using a strong visible light source.

As an alternative to dissolving the heavy metal organic compound in monomer(s) followed by polymerization, the homogeneous organometallic-polymer composites may be formed by film casting methods and solvent evaporation. Incorporation of triphenyl bismuth, for instance, in poly(methyl methacrylate) to form films or transparent radiopaque shields can be performed by dissolving the polymer and heavy metal compound in a common solvent like THF. Thus, for example 40 percent by weight solution of triphenyl bismuth in THF containing dissolved poly(methyl methacrylate) can be cast as a film and the solvent allowed to slowly evaporate.

Another alternative for making homogeneous, radiopaque composites is by thoroughly mixing the heavy metal organic compound with the polymer, followed by melting processing of this mixture. For example, mixtures of triphenyl bismuth and powdered polypropylene, when heated above the melting point of the polymer produce homogeneous, radiopaque composites.

Radiopaque polyesters of the present invention may be prepared by dissolving the heavy metal organic compound in a polyol, such as, for example, ethylene glycol. The dissolved organometallic compound is then mixed with a dicarboxylic acid, such as terephthalic acid or phthalic anhydride, and polymerized at elevated temperatures in the presence of a known catalyst.

As previously mentioned, the radiopaque heavy metal compound polymer composites have a wide variety of applications especially in the dental and medical field. In the latter, the radiopaque polymers may be employed in resin systems having low levels of cross-linking which, for purposes of the present invention, range from 0 to about 5 percent, and denser more rigid structures having a higher degree of cross-linking ranging from more than 5 to about 15 percent. Such systems include "self-curing" type resins which react at ambient temperatures of between 25° and 30° C., and systems which cure at elevated temperatures with the application of heat.

Generally, for preparing radiopaque biomedical resins, i.e., polymer compositions having useful applications in restorative dentistry and medicine, the heavy metal-polymer composite would be ground to a fine powder and used as a component of a two-part system. More specifically, in the two-part system the composition is furnished in two separate containers. The first container would comprise a powder containing a mixture of the radiopaque polymer complex previously described, fillers and an initiator, such as benzoyl peroxide or AIBN. The second container comprises a liquid containing methyl methacrylate monomer, an amine accelerator and a cross-linking agent such as ethylene glycol dimethacrylate. When the solutions are mixed, or when in the absence of amine accelerator they are exposed to a strong visible light, the radiopaque polymer complex will swell in the methyl methacrylate monomer and polymerize into a solid homogeneous polymeric mass.

Applications for the radiopaque polymer composites having low levels of cross-linking include removable dental devices like dentures, bite splints, night guards, orthodontic space maintainers, maxillofacial devices and other nonfixed devices where there is a risk of accidental impaction into the respiratory or digestive tracts. These radiopaque polymer composites having low levels of cross-linking can also be formulated into bone cements for bonding implanted devices to bone tissues so as to permit monitoring by noninvasive methods.

The second category for biomedical resins include highly cross-linked structures where radiopacity is also a desirable property. They include fixed structures like restorative resins, veneering facings for dental crowns and bridges, dental and surgical implants, root canal sealants and other dental, surgical and implants applications. These materials are generally provided to the user as a two-part system which upon mixing cures at ambient temperatures either by combining the initiator with a light source or with an amine accelerator. In the highly cross-linked structures, however, no preformed polymer is used. Instead, each component consists of a solution of monomers. Many of such applications can also employ a hard, inert reinforcing "filler" consisting of a finely divided material such as silica.

In addition to the foregoing medical/dental applications, the radiopaque polymer composites may be used with all body implants, prosthetic devices and appliances which are presently used with radiolucent plastics, such as, for example, catheters, bone implants, heart valves or arteries.

Industrial applications for the radiopaque composites of the present invention include x-ray and other radiation shielding devices. Optionally, the transparent radiopaque polymers, which are also opaque to U/V radiation, can be used in such areas as aircraft windows and cabins for shielding pilots and astronauts from high energy U/V and x-radiation found at high altitudes. Transparent shielding devices made of sheets of radiopaque plastics for workers exposed to x-rays and other forms of potentially harmful radiation are also intended utilities. The radiopaque polyester fibers are especially useful in textiles and fabrics for making specialized radiopaque garments to be worn by workers exposed to radiation in the job place.

Additionally, the radiopaque polymers can be incorporated into any plastic device which requires detection by x-rays. For example, the composites of this invention can be incorporated into plastic firearms to ensure detection by airport security x-ray devices.

The following specific examples demonstrate the radiopaque polymers and resin compositions, and are representative of the various methods for producing them. However, it is to be understood that these examples are for illustrative purposes only and do not purport to be wholly definitive as to conditions and scope.

EXAMPLES I–VII

Seven samples of the composites of this invention were prepared by dissolving varying concentrations of triphenylbismuth in methyl methacrylate monomer. The compositions are reported in Table A. AIBN or BPO was added as an initiator in an amount of 0.5% by weight based on the monomer. Each sample was placed in a test tube with a serum cap, flushed with nitrogen, sealed and bulk polymerized for 48 hours at 65° C. All samples of methyl methacrylatetriphonylbismuth formed a hard, transparent, colorless, clear and homogenous polymer.

The radiopaque polymers of Examples I–VII were tested to develop data on the possible presence of free triphenylbismuth and the effects of dissolved triphenyl bismuth on the glass transition temperature of poly(methyl methylacrylate) by differential scanning calorimetry using a Perkin-Elmer DSC-4 instrument. Scans were run from 50° to 150° C. with a scan rate of 20° C. per minute. A sample of poly(methyl methylacrylate) containing no triphenylbismuth was used as a control for comparison purposes. The results of the DSC analyses are also reported in Table A.

TABLE A

| | Triphenylbismuth Weight % | Tg °C. |
|---|---|---|
| Control | 0.0 | 117 |
| Example I | 0.51 | 117 |
| Example II | 1.17 | 115 |
| Example III | 6.8 | 106 |
| Example IV | 10.6 | 101 |
| Example V | 17.9 | 91 |
| Example VI | 26.5 | 85 |
| Example VII | 32.1 | 75 |

The data in Table A show a gradual decrease in the glass transition temperature on increasing the triphenylbismuth content. The 78.5° C. melt peak of triphenyl bismuth was not evident in any sample. Thus, a homogenous dispersion of triphenylbismuth in polymer was formed.

The radiopacity of the composites of EXAMPLES I–VII was tested as follows: Samples of EXAMPLES I–VII were cut in cylindrical pellets of I mm and 2 mm thickness. The pellets were polished and placed on a Kodak X-ray film along with an aluminum stepwedge with 1mm steps. The pellets were placed 22 inches below the cathode ray tube of an X-ray apparcitus and exposed to 90 kv 6 ma X-rays. Using a microfilm densitometer the X-ray absorption of the pellets was then compared with that of the aluminum stepwedge. It was found that 23 percent by weight triphenyl bismuth was required in a 2 mm pellet to provide the same radiopacity as a 2 mm pellet of aluminum, a radiopacity standard adopted for dental applications.

Studies were also performed to determine the leachability, heat stability, and air and moisture sensitivity of the samples prepared in Examples I–VII. The composite samples were placed in a tube which was sealed. Vacuum was applied and the samples were heated up to 150°–160° C., which temperature was maintained for several hours. No change in color, transparency or homogeneity was observed in the samples. In addition, samples of the composites of EXAMPLES I–VII were placed in water for more than 4 months. No change in color, transparency, homogeneity, radiopacity or weight of the samples was observed. No detectable amount of triphenylbismuth was found in the water. All the experiments show non-leachability, heat stability, moisture and air insensitivity of the polymer-triphenylbismuth system made in accordance with the present invention.

EXAMPLE VIII

Room temperature polymerization in accordance with this invention was performed by dissolving the organometallic compound in the monomer, followed by addition of an initiator and an amine accelerator to form the polymer-organometallic composite. As a specific example, the composite of EXAMPLE VIII was prepared according to the following procedure: in a test tube 0.25 grams of triphenylbismuth was dissolved in 0.9 grams of methyl methacrylate to form a clear, homogeneous and transparent solution. Benzoylperoxide, an initiator, was then added to the mixture in an amount of 0.025 grams or 2.5 weight percent based on the monomer. By adding 0.015 grams of an amine accelerator, specifically, N,N-dimethyl p-toluidine, a hard, polymerized, homogeneous, transparent product was formed after a few minutes. The composites of Examples VIII had the same mechanical and thermal stability, and the same air and moisture insensitivity as the composites formed in Examples I–VII.

EXAMPLES IX and X

Another way of incorporating organometallic compounds into polymers is by solvent casting and formation of transparent and clear homogeneous films. In Examples IX and X the incorporation of triphenylbismuth into poly(vinyl chloride) was achieved by dissolving polyvinylchloride in hot THF (50°–55° C.) in a test tube. After complete dissolvation, triphenylbismuth was added and the solution stirred for about 1 hour. The colorless, clear, homogeneous solution formed was poured into a glass dish. The THF was removed first under a flow of $N_2$ for 48 hours and then in a vacuum oven until a constant weight for the film was achieved. PVC used in this experiment had a molecular weight of about 93,000.

| Formulation of EXAMPLES IX and X | | |
|---|---|---|
| | | Wt % |
| Example IX | | |
| Polyvinylchloride | 0.161 gm | 72 |
| Triphenylbismuth | 0.062 gm | 28 |
| THF | 0.2 ml | |
| Example X | | |
| Polyvinylchloride | 0.17 gm | 84.5 |

-continued

| Formulation of EXAMPLES IX and X | | |
| --- | --- | --- |
| | | Wt % |
| triphenyl bismuth | 0.032 gm | 15.5 |
| THF | 0.2 ml | |

The films formed by this method were transparent, clear and homogeneous. IR spectra of the samples of Examples IX and X show no trace of solvent (THF) left in the film.

The solvent casting procedure may be used to incorporate organometallic compounds into many other polymers. The choice of solvents is dependent on the solubility of the polymers and organometallic compounds in the solvents. For example, an appropriate solvent for incorporating triphenylbismuth into polyacrylonitrile by solvent casting is dimethyl formamide (at 70° C.), and for preparing polyethylene-triphenylbismuth composites hexane is an appropriate solvent.

EXAMPLES XI–XIV

Radiopaque characteristics may also be imparted to polymers according to this invention by compounding polymer and an organometallic compound followed by melt processing to incorporate heavy metal organometallic compounds into polymers.

The composites of EXAMPLES XI–XIV were prepared by first mixing (compounding) the triphenylbismuth into isotactic polypropylene and then transferring the mixture to a test tube. The mixture is sealed and the test tube is evacuated. The mixture is heated above its melting point and kept at that temperature for a few hours to give a homogeneous, clear and transparent mixture. The mixture on cooling becomes opaque, as is pure isotactic polypropylene. The weight percent of triphenylbismuth in isotactic polypropylene for EXAMPLES XI-XI aree shown in TABLE B.

The isotactic polypropylene-triphenylbismuth samples of EXAMPLES XI–XIV were cut in cylindrical pellets of 1 mm and 2 mm thickness. The radiopacity of the samples was measured the same way as described above in regards to EXAMPLES I–VII of this invention. It was found that 35 percent by weight triphenyl bismuth was required in a 2 mm pellet to provide the same radiopacity as a 2 mm pellet of aluminum.

The thermal properties of the samples of EXAMPLES XI–XIV were tested using the procedures described above in regard to EXAMPLES I–VII. The control in this case is pure isotactic polypropylene. The results are also shown in TABLE B.

TABLE B

| | Weight percent of Triphenyl bismuth | $T_m$ °C. |
| --- | --- | --- |
| Control | 0.0 | 152 |
| EXAMPLE XI | 10 | 151 |
| EXAMPLE XII | 15 | 150 |
| EXAMPLE XIII | 25 | 146 |
| EXAMPLE XIV | 30 | 146 |

DSC measurements of the blends show no melting point for triphenylbismuth indicating a homogeneous composite was achieved. Other than radiopacifying properties of these blends, the composites of EXAMPLES XI–XIV are heat stable, non-leachable and moisture and air insensitive.

EXAMPLE XV

Diphenyl p-styryl bismuth, synthesized according to known procedures, was copolymerized with methyl methacrylate in bulk with AIBN at 65° C. to give a transparent, hard and clear copolymer. Because the monomer-containing heavy metal is part of the backbone of the product, it improves the thermal and mechanical properties of polymers in comparison to materials containing heavy metal components as additives only. Its permanent, chemical incorporation into the polymer structure prevents the leaching out of the heavy metal X-ray contrast agent in any kind of solvent.

| Formulation of EXAMPLE XV | |
| --- | --- |
| Diphenyl p-styryl bismuth | 0.54 gram |
| Methyl methacrylate | 1.26 gram |
| AIBN | .009 gram |

As should be apparent to those skilled in the art, the same procedure may be followed to achieve copolymerization with other monomers.

Other copolymers were formed using the same procedure given for EXAMPLE XV to yield poly(methylmethacrylate-codiphenyl p-styryl bismuth) with different weight percent (or molar ratio) of heavy metal monomer. These copolymers were cut in cylindrical pellets of 1mm and 2 mm thickness. The radiopacities of the pellets, were measured the same way as mentioned above in regard to Part C Examples I-VII of this invention. It was found that for this copolymer a 2 mm thick pellet containing 26 wt % of the bismuth-containing monomer gave the same radiopacity as 2 mm thick aluminum. The Tg of this copolymer was 110° C., close to that of pure poly(methylmethacrylate), a considerable improvement of the Tg of 85° C. (Table A, Example VI) for a composite of poly (methyl methacrylate) and triphenylbismuth.

EXAMPLE XVI

The organometallic radiopacifying compounds including the radiopacifying monomers of this invention do not interfere with room cured polymerization procedures utilizing amine accelerators. EXAMPLE XVI was prepared by the room temperature polymerization of methyl methacrylate which contained 30 weight percent of diphenyl p-styryl bismuth in accordance with the procedure described above with regard to EXAMPLE VIII of this invention.

| Formulation of EXAMPLE XVI | |
| --- | --- |
| Diphenyl p-styryl bismuth | 0.54 g |
| methyl methacrylate | 1.26 g |
| Benzoyl peroxide | 0.045 g |
| N,N-dimethyl p-toluidine | 0.027 g |

The copolymer formed by this method has the same transparency, homogeneity, and mechanical and thermal properties as that formed in EXAMPLE XV of this invention.

Although particular illustrative embodiments of the present invention have been described herein, the present invention is not limited to these particular embodiments. Various changes and modifications may be made thereto by those skilled in the art without departing from the spirit or scope of the invention, which is defined by the appended claims.

We claim:

1. A solid, optically lucent radiopaque composition comprised of a polymer and an organometallic compound which is triphenyl bismuth, said organometallic compound being soluble in said polymer or in a monomer from which said polymer can be formed and present in said composition in an amount from about 5 to 70 weight percent; and said organometallic compound being homogeneously distributed in the polymer at the molecular level.

2. The radiopaque composition of claim 1 wherein the organometallic compound is present in an amount sufficient to impart to said composition at least the same radiopacity as aluminum.

3. The radiopaque composition of claim 1 wherein said organometallic compound is present in an amount greater than about 23 weight percent.

* * * * *